United States Patent [19]

Ai et al.

[11] Patent Number: 4,909,738
[45] Date of Patent: Mar. 20, 1990

[54] ARTIFICIAL TEETH FOR ANTERIOR TEETH PORTIONS

[75] Inventors: Minoru Ai, Tokyo; Kensuke Yamagata, Kawasaki; Tadaki Kagaya, Tokyo; Akira Hasegawa, Inuyama; Yuji Nakamura; Ikuo Ikeda, both of Kasugai, all of Japan

[73] Assignee: G-C Toshi Kogyo Corporation, Kasugai, Japan

[21] Appl. No.: 384,482

[22] Filed: Jul. 25, 1989

[30] Foreign Application Priority Data

Aug. 12, 1988 [JP] Japan .............................. 63-200084

[51] Int. Cl.⁴ .............................................. A61C 13/08
[52] U.S. Cl. .................................. 433/202.1; 433/218
[58] Field of Search ................... 433/202.1, 203.1, 204, 433/212.1, 218, 219

[56] References Cited

U.S. PATENT DOCUMENTS

| | | | |
|---|---|---|---|
| 1,172,652 | 2/1916 | Whiteside | 433/204 |
| 2,310,732 | 2/1943 | Dietz | 433/207 |
| 3,052,982 | 9/1962 | Weinstein et al. | 433/206 |
| 3,488,847 | 1/1970 | Pettrow | 433/212.1 |
| 4,645,455 | 2/1987 | Kosmos | 433/203.1 |

Primary Examiner—John J. Wilson
Attorney, Agent, or Firm—Oblon, Spivak, McClelland, Maier & Neustadt

[57] ABSTRACT

An artificial tooth for anterior teeth portions including a concave hollow extending from a basal segment to a lingual incisal segment and located in a substantially central segment, wherein: a percentage of the major diameter of the hollow to the full length is in a range of 10% to 100%, a maximum depth of the hollow is in a range of 0.5 mm to 5.0 mm and a minimum thickness of a cervical segment is in a range of 0.1 mm to 5.0 mm, and a width and length of the cervical segment being defined in terms of a percentage of the cervical minimum mesiodistal length to the maximum mediodistal length being in a range of 50% to 100% and a percentage of the cervical major diameter to the full major diameter being in a range of 10% to 50%.

4 Claims, 2 Drawing Sheets

ARTIFICIAL TEETH FOR ANTERIOR TEETH PORTIONS

BACKGROUND OF THE INVENTION

1. Field of the Invention

The present invention relates to artificial teeth for anterior teeth portions which are formed of any one of synthetic resin, ceramics and a composite material of synthetic resin with ceramics, and are of a structure and geometry especially suitable for the preparation of partial dentures or overdentures.

2. Statement of the Prior Art

Partial dentures or overdentures are an intra-oral removable type of prostheses applied to a wide variety of teeth-deficient states from the failure of one tooth to the remaining of one tooth. These dentures are much more frequently used as compared with complete dentures, and are thus said to account for approximately 80% of all the dentures now available. The purpose of such dental prostheses is generally broken down into the following four aspects:

(1) Recovery and Amelioration of Aesthetic Appearance.
(2) Recovery and Amelioration of Masticatory Function.
(3) Recovery and Amelioration of Pronouncing Function.
(4) Retainment and Recovery of Sound Intra-Oral Tissue.

In particular, the failure of anterior teeth portions with or without a molar deficiency has relation to not only the recovery and amelioration of masticatory function but the rest of the items as well. The recovery and amelioration of aesthetic appearance, which are of course in touch with the face and the recovery and amelioration of dentition, have an intermediate influence upon the mental and physical aspects of patients and affect seriously the rapid mesial migration of distal teeth into a void space. The anterior teeth play an important role in the recovery and amelioration of pronouncing function, because the amelioration of dental and labiodental sounds or the recovery of dyslalia is achieved by prostheses applied to the failed anterior teeth. Referring to the retainment and recovery of sound intra-oral tissue, it is well known that the failure of teeth and a functional occlusion allow the retroplasia and pathema of intra-oral tissue to go wrong. Thus, the prostheses for failed teeth are also important in view of the prevention of such retroplasia. In view of the foregoing, the partial dentures or overdentures are very important prostheses. Since such prostheses are removable in the oral cavity as mentioned above, it is a requisite for them to comprise the following elements.

(1) Retainers (clasps, attachments, telescopes, etc.).
(2) Connectors.
(3) Artificial Teeth.
(4) Dental Plates.

Of these elements, the retainers, connectors and dental plates should be designed taking into consideration various factors such as the teeth to be retained, the ridge muscles of mastication, the temporomandibular joint and the patient's interest in the intra-oral cleanness. In the selection and alignment of artificial teeth, they are required to be designed depending upon the state of the remaining teeth or the teeth to be retained, while taking into consideration their size, geometry, color tone, direction, proximal relation, occlusal relation, etc. Numerous studies have been made of such retainers, connectors and dental plates, but never before have any studies been made of the structure and geometry of artificial teeth to be used as the anterior teeth portions of partial dentures. Artificial teeth designed for complete dentures are thus still unavoidably used to this end.

However, the following problems arise when the conventional artificial teeth for anterior teeth portions designed for complete dentures are used as parts of partial dentures or overdentures.

(1) In order to make partial dentures or overdentures, it is required to use artificial teeth in combination with a retainer, a connector and a dental plate (especially a metal plate) and so provide therein a space for receiving them. This inevitably requires to cut off a portion of the basal plane of each artificial tooth. Consequently, not only does it take some time to make partial dentures or overdentures but it is also likely that the configurations of the artificial teeth may deform without recourse to versed skill.

(2) If partial dentures or overdentures are made by cutting off a portion of the basal plane of the conventional artificial teeth for anterior teeth portions designed for complete dentures, it is then impossible to obtain the color tone inherent in the artificial teeth. Besides, the retainer and connector as well as the dental plate (especially a metal plate) are seen through. The reasons are that while the conventional artificial teeth for anterior teeth portions designed for complete dentures comprise a three-layered system of enamel, dentine and cervical layers or two-layered system of enamel and dentile layers, it is likely that the cutting of their basal planes may remove all the dentine and cervical layers or the whole cervical layer and a part of the dentine layer, and if necessary even a part of the enamel layer.

(3) In most cases, the conventional artificial teeth for anterior teeth portions used for complete dentures are designed to be used with dental plates joined thereto, so that their cervical segments are made narrow as viewed in the mesiodistal direction and their major diameters are considerably short. Thus, when used as partial dentures or overdentures, they tend to become aesthetically unnatural because of a gap between the interdental pappilae and trap food tailings or dental plaque therein. A short cervical segment, as viewed in the major-diameterical direction, tends to become unfit for the face and age due to lack of no harmony with the remaining teeth suffering from gingival retraction.

SUMMARY OF THE INVENTION

An object of the present invention is to provide an artificial tooth for anterior teeth portions which eliminates all the disadvantages of the conventional artificial teeth for anterior teeth portions.

According to the present invention, this object is achieved by the provision of an artificial tooth for anterior teeth portions including a concave hollow extending from a basal segment to a lingual incisal edge segment and located in a substantially central segment, wherein:

a percentage of the major diameter of said hollow to the full length is in a range of 10% to 100%, a maximum depth of a cervical segment is in a range of 0.5 to 5.0 mm, and a minimum thickness of a cervical segment is in a range of 0.1 mm to 5.0 mm, and a width and length of said cervical segment being defined in terms of a percentage of the cervical minimum mesiodistal length to the maximum mesiodistal length being in a range of 50% to 100% and a percentage of the cervical major diameter to the full major diameter being in a range of 10% to 50%.

Reference will now be made specifically to how to eliminate the individual disadvantages of the prior art.

(1) For the preparation of partial dentures or overdentures, there is a need to combine artificial teeth with rests, retainers, connectors and dental plates (especially metal plates). This then requires to provide therein a space for such purposes and, hence, to cut a part of the basal plane of each artificial tooth. Especially when the retainer is in the form of a attachment, it is necessary to use an artificial tooth hollowed to wrap the attachment with the teeth to be retained. When a clasp or telescope is used as the retainer, it is necessary to use an aritificial tooth hollowed in a region corresponding to a labial or buccal side of a sort of a cast crown used to retain it. However, since each of the present artificial teeth for anterior teeth portions has a hollow previously formed in its basal plane, there is no need to cut that basal place, as experienced with the conventional artificial teeth for anterior teeth portions designed for complete dentures. This leads to a reduction in the total operating time, since there is no need to cut the basal plane of each artificial tooth. Furthermore, it is possible to prepare partial dentures or overdentures without being affected by versed skill needed for the cutting of the basal planes of artificial teeth and giving rise to any deformation of the configurations of artificial teeth.

(2) Since the need of cutting the basal planes of artificial teeth is eliminated considerably by the use of the artificial teeth for anterior teeth portions according to the present invention, it is possible to keep the natural color tone inherent thereto. Besides, it is unlikely that a retainer or connector and a dental plate (especially a metla plate) may be seen through the two-layered system of enamel and dentine layers or three-layered system of enamel, dentine and cervical layers owing to the hollow structure.

(3) With the present artificial teeth for anterior teeth portions wherein the percentage of the cervical minimum mesiodistal length to the maximum mesiodistal length is as high as 50 to 100%, it is less likely that food tailings forming dental plaque may remain in the interdental pappilae due to a decreased gap therebetween, as compared with the conventional artificial teeth for anterior teeth portions designed for complete dentures. The present artificial teeth for anterior teeth portions, wherein the percentage of the cervical major diameter to the full major diameter is between 10% and 50%, are in much well-balanced harmony with the remaining teeth suffering from gingival retraction and give a highly improved natural looks in terms of face and age.

BRIEF DESCRIPTION OF THE DRAWINGS

The present invention will now be explained in more detail with reference to the accompanying drawings, which are given for the purpose of illustration alone, and in which.

DETAILED EXPLANATION OF THE PREFERRED EMBODIMENT

Figure 1:
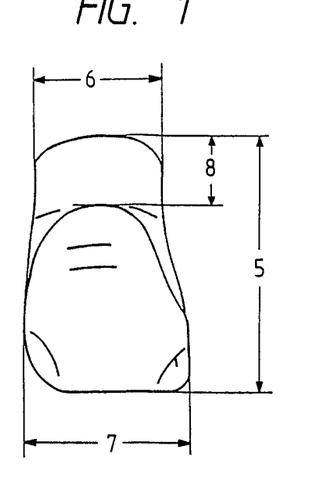
FIG. 1 is a front view of one embodiment of the maxillary right-central incisor of the artificial teeth for anterior teeth portions according to the present invention.
Figure 2:
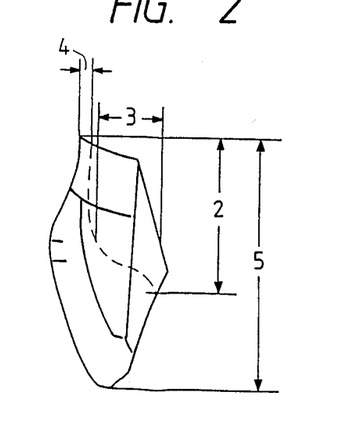
FIG. 2 is a side view of that incisor.
Figure 3:
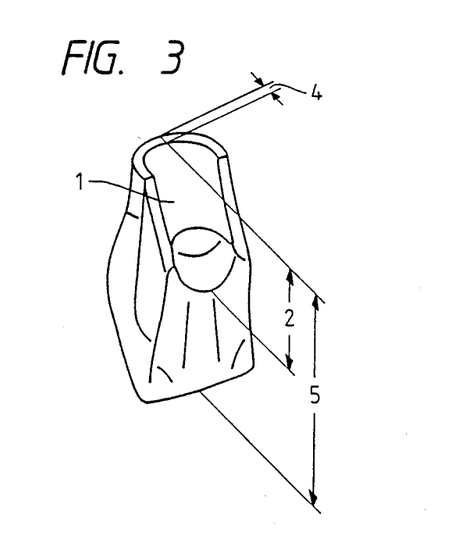
FIG. 3 is a perspective view of that incisor.
Figure 4:
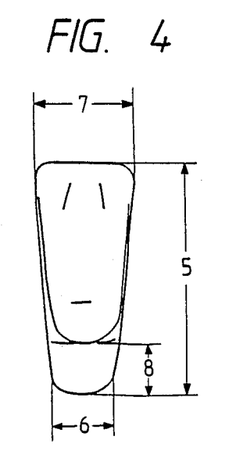
FIG. 4 is a front view of one embodiment of the mandibular right-central incisor of the artificial teeth for anterior teeth portions according to the present invention.
Figure 5:
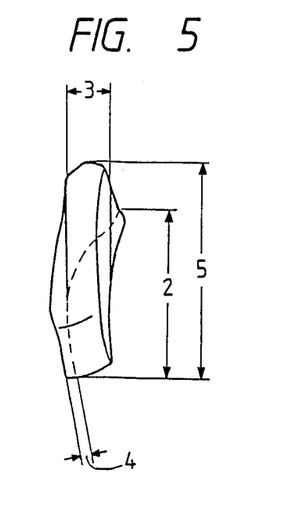
FIG. 5 is a side view of that incisor.
Figure 6:
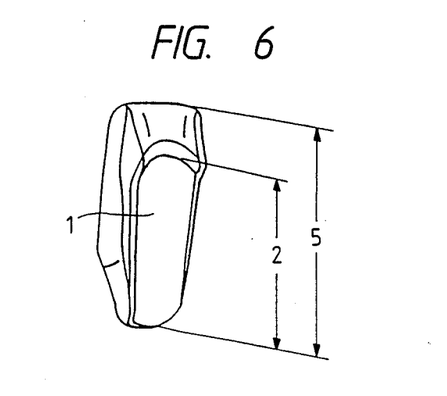
FIG. 6 is a perspective view of that incisor.

Referring to FIGS. 1 to 6, there are illustrated preferred structures of the artificial teeth for anterior teeth portions according to the present invention, which are well-suited for making partial dentures or overdentures. As illustrated in FIGS. 1 and 6, there is provided a hollow 1 defining a space for receiving a retainer, a connector or the like. The hollow 1 has a major diameter shown at 2 and a maximum depth shown at 3, and a cervical segment has a minimum thickness shown at 4. Reference numeral 5 stands for a full length of the tooth, 6 a minimum mesiodistal length, 7 a maximum mesiodistal length and 8 a major diameter of the cervical segment. The major length 2 and maximum depth 3 of the hollow 1 affect elementarily the space for receiving the retainer and connector; the minimum thickness 4 of the cervical segment affects the retainment of the inherent natural tone of color, a shielding effect on a metallic retainer or connector and a metallic plate and the mechanical properties of the artificial teeth per se; the minimum mesiodistal length 6 of the cervical segment affects the size of the interdental pappilae, i.e., an aesthetic aspect and an oral-hygienical aspect for eliminating a tendency for food tailings to remain in the oral cavity; and the major diameter 8 of the cervical segment affects a harmony with the remaining teeth, while taking the face or age into consideration.

According to the present artificial teeth for anterior teeth portions, the maximum hollow depth 3 is 0.5 mm or longer and 5.0 mm or shorter, while taking into consideration the sizes of various retainers, connectors and the like. At 0.5 mm or shorter, the space for receiving various retainers, connectors or the like becomes so insufficient that there is a need of carrying out additional cutting of the basal plane of the artificial tooth, and this is disadvantageous in that the length of time required for dental operations may be increased or the configuration of the artificial tooth may deform. At 5.0 mm or longer, the labiolingual length increases inevitably, leading to an increased feeling of incompatibility during wear. Then, the percentage of the major diameter 2 to the full length 5 is 10% or higher and 100% or less. At 10% or lower, the space for receiving various retainers, connectors or the like tends to be insufficient. It is noted that a figure 100% indicates that the hollow 1 may extend from the labiocervical segment to the incisal edge segment. The minimum thickness 4 of the cervical segment is 0.1 mm or longer and 5.0 mm or shorter. At 0.1 mm or shorter, a shielding effect on metallic retainers or connectors or metallic plates is so poor that they may be seen through. What is more, the strength and wear resistance of the artificial tooth per se are adversely affected. At 5.0 mm or longer, if it is intended to eliminate a sense of incompatibility during wear while taking the maximum depth 3 into consideration, the maximum depth 3 then decreases, thus making narrower the space for receiving various retainers, connectors and the like. On the contrary, if the maximum depth 3 is enough to take an ample space for receiving various retainers, connectors or the like, the labiolingual diameter of the tooth then increases, resulting in an increased sense of incompatibility during wear. The percentage of the minimum mesiodistal length 6 of the cervical segment to the maximum mesiodistal length 7 is 50% or higher 100% or less. At 50% or lower, there is an increase in the gap between the interdental pappilae and this is unpreferred in view of oral hygiene since food tailings tend to remain there, thus forming dental plaque. At 100% or higher, the mesiodistal length of the incisal edge segment is shorter than that of the cervical segment. As a result, when the artificial teeth are aligned in order, the resulting alignment of teeth is considerably unnatural and aesthetically poor, although there is formed no gap between the interdental pappilae. The percentage of the major diameter 8 of the cervical segment to the full length 5 is 10% or higher and 50% or lower. At 10% or lower, there are obtained juvenile teeth, which are in ill-harmony with the remaining teeth suffering from gingival retraction and, hence, unnatural looks for the face and age. At 50% or higher, an aesthetic problem arises due to too long a cervical segment, even taking into consideration a harmony with the remaining teeth suffering from gingival retraction. If however such an artificial tooth is unavoidably used, then its long cervical segment should be cut to a suitable length.

The present artificial teeth for anterior teeth portions suitable for making partial dentures or overdentures may be formed of synthetic resin, ceramics or a composite material of synthetic resin with ceramics. The synthetic resins used may include methyl methacrylate, ethyl methacrylate, isopropyl methacrylate, hydroxyethyl methacrylate, tetrahydrofurfuryl methacrylate, glycidyl methacrylate, 2,2-bis(methacryloxyphenyl)-propane, 2,2-[4-(2-hydroxy-3-methacryloxyethoxyphenyl)]propane, 2,2-bis(4-methacryloxyethoxyphenyl)propane, 2,2-bis(4-methacryloxydiethoxyphenyl)propane, 2,2-bis(4-methacryloxypropoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritol tetramethacrylate and related acrylates. These monomers may be used alone or in combination of two or more and crosslinked. For use, all the monomers are polymerized with an organic peroxide such as benzoyl peroxide, an azo compound such as azobisisobutylonitrile, a pyrimidine trion derivative such as 1-cyclohexyl-5-ethylpyrimidine trion. Alternatively, the above monomers may be mixed with organic powders and then polymerized for use. The organic powders used to this end may include polyolefin powders (such as polyethylene or polypropylene powders), polyacrylate ester powders (such as methyl or ethyl polymethacrylates), polymethacrylate ester powders (such as methyl and ethyl polymethacrylates), acrylate ester polymer powders (such as copolymers of methyl polyacrylate with ethyl polyacrylate), methacrylate ester polymer powders (such as copolymers of methyl polymethacrylate with ethyl polymethacrylate), crosslinked type polymethacrylate ester powders (such as methyl polymethacrylate crosslinked with trimethylolpropane trimethacrylate), styrene/butadiene copolymer powders, styrene powders, styrene/methyl polymethacrylate copolymer powders, acrylonitrile/styrene copolymer powders, acrylonitrile/styrene/butadiene copolymers and nylon powders. These materials may be used alone or in the form of mixture of two or more thereof.

The ceramic materials used may include alumina, magnesia, calcia, zirconia, silica, forsterite, steatite, wollastonite, zircon, mullite, cordierite, spodumene, aluminium titanate, spinel, apatite, boron oxide, silicon nitride, aluminium nitride, boron nitride, titanium nitride, silicon carbide, boron carbide, titanium carbide, tungsten carbide and lithium oxide. These materials may be used alone or in the form of a mixture, compound or solid solution of two or more thereof, and may be either crystalline or amorphous.

The composite materials of synthetic resin with ceramics used may include grain-dispersed type composite materials, short fiber-reinforced type composite materials, laminates and interpenetrating network composites of the aforesaid synthetic resins and ceramics. The reinforcing materials other than the aforesaid ceramics may include alumina whiskers, beryllium oxide whiskers, boron carbide whiskers, silicon carbide whiskers, silicon nitride whiskers and various metal whiskers as well as the so-called organic composite fillers obtained by compacting and powdering colloidal silica with the use of polymers. It is desired that such ceramic reinforcements, various metal whiskers and organic composite fillers are treated with coupling agents to increase their adhesion to the synthetic resins. The coupling agents used may include organofunctional silane coupling agents, titanate coupling agents, zircoaluminate coupling agents and the like. The ceramics may be grafted on their surfaces to increase their adhesion to the synthetic resins.

Examples

The present inventiin will now be explained specifically but not exclusively with reference to the following examples and comparison examples.

Several aspects were estimated as follows. In the table to be given later, the results of the examples and comparison examples are summarized.

(1) Space for Retainer or Connector

A crown attachment was used as the retainer. Its female segment was attached to a pier tooth and its male segment was joined to an artificial tooth. Estimation was then made on whether or not there was a hollow space sufficient to receive the crown attachment. For a teeth-deficient region, artificial teeth were aligned on the labial side with a cast connector post, and GC Thermoresin LC (a light-cured resin for crowns and bridges manufactured by GC Dental) was filled-in from the lingual side to wrap the post therewith, followed by about 40-second irradiation with GC Light VL-I (a visible light irradiator manufactured by GC Dental) for polymerization and fixation. Estimation was then made on whether or not there was a hollow space sufficient to wrap the post.

(2) Color Tone of Artificial Teeth

The artificial teeth for anterior teeth portions were combined with a retainer or connector. Visual estimation was then made on whether or not their color tone was similar to that of conventional artificial teeth. For the artificial tooth for comparison purposes, the lingual basal plane of which had to be cut for combination with a retainer or connector, its color tone was visually estimated after cutting.

(3) Shielding Effect on Metal

In a similar manner as mentioned in connection with "Color Tone", visual estimation was made on whether or not the metal was seen through the labial side.

(4) Strength of Cervical Segment

Depending upon the thickness of the cervical segment, the artificial tooth for anterior teeth portions according to the present invention may be lacking in strength owing to the presence of a hollow. Estimation was then made on whether or not the cervical segment was broken upon firmly clamped by the thumb and first finger. For the artificial tooth for comparison purposes, the lingual basal plane of which had to be cut for combination with a retainer or connector, similar estimation was made after cutting.

(5) Remaining of Food Tailings Between Interdental Pappilae

Partial dentures were made in various forms of three teeth, i.e., the maxillary right-central incisor, right-lateral incisor and right-lateral cuspid, and then used by the same patient one for every week. Inquiry estimation was then made on whether or not there were food tailings in the interdental pappilae between the maxillary right-centeral incisor and right-lateral incisor and between the maxillary right-lateral incisor and the maxillary right-lateral cuspid.

(6) Harmony with Remaining Teeth of Patients Suffering from Gingival Retraction

Various forms of the artificial teeth for anterior teeth portions were used by patients suffering from gingival retraction. Visual estimation was then made on the color and geometrical harmonies with the remaining teeth.

(7) Feeling of Intra-Oral Incompatibility

Partial dentures made with various artificial teeth for anterior teeth portions were used by the same patient one for every week. Oral inquiry estimation was then made on a feeling of incompatibility.

(8) Total Dental-Operating Time

Estimation was made on the dental-operating time required to make partial dentures with the artificial teeth for anterior teeth portions. The operating time was defined by the time for the preparation of a stone to include waxing-up, investing, casting, polishing, joining of artificial teeth and wearing.

TABLE

| | Artificial Teeth | Material | $\frac{\text{Major diameter of hollow}}{\text{Full length}} \times 100$ (%) | Maximum depth of hollow (mm) | Minimum thickness of cervical segment (mm) | $\frac{\text{Cervical minimum mesiodistal length}}{\text{Maximum mesiodistal length}} \times 100$ (%) | $\frac{\text{Major cervical diameter}}{\text{Full length}} \times 100$ (%) |
|---|---|---|---|---|---|---|---|
| Example 1 | Maxilliary right-central incisor | Synthetic resin | 63 | 2.5 | 1.8 | 82 | 21 |
| Example 2 | Maxilliary right-lateral incisor | Synthetic resin | 100 | 1.6 | 1.1 | 88 | 17 |
| Example 3 | Maxilliary right cuspid | Synthetic resin | 18 | 3.2 | 1.8 | 87 | 27 |
| Example 4 | Maxilliary right-central incisor | Synthetic resin | 66 | 4.2 | 0.3 | 86 | 25 |
| Example 5 | Maxilliary right-central incisor | Ceramics | 73 | 0.9 | 4.0 | 90 | 21 |
| Example 6 | Maxilliary right cuspid | Ceramics | 60 | 3.2 | 1.8 | 100 | 20 |
| Example 7 | Mandibular right-central incisor | Ceramics | 68 | 1.4 | 1.2 | 64 | 23 |
| Example 8 | Mandibular right-central incisor | Composite material | 68 | 1.5 | 1.2 | 85 | 40 |
| Example 9 | Mandibular right-central incisor | Composite material | 69 | 1.5 | 1.2 | 82 | 8 |
| Comparative Example 1 | Maxilliary right-central incisor | Synthetic resin | 7 | 2.5 | 2.0 | 82 | 22 |
| Comparative Example 2 | Maxilliary right-central incisor | Synthetic resin | 60 | 5.5 | 0.08 | 88 | 25 |
| Comparative Example 3 | Maxilliary right cuspid | Synthetic resin | 65 | 0.4 | 5.0 | 90 | 21 |
| Comparative Example 4 | Maxilliary right-lateral | Ceramics incisor | 76 | 2.8 | 1.6 | 105 | 21 |
| Comparative Example 5 | Mandibular right-central incisor | Ceramics | 66 | 1.4 | 1.1 | 30 | 29 |
| Comparative Example 6 | Mandibular right-central incisor | Composite material | 60 | 1.4 | 1.2 | 84 | 60 |
| Comparative Example 7 | Mandibular right cuspid | Synthetic resin | 68 | 1.5 | 1.2 | 88 | 3 |
| Comparative Example 8 | Maxilliary right-central incisor | Synthetic resin | No hollow | No hollow | 1.2 | Due to forming a circular arc, the minimum mesiodistal length of the cervical segment cannot be measured | 9 |

| | Space for retainer or connector | Colortone of artificial teeth | Shielding effect on metal | Strength of Cervical segment | Remaining of food tailings between interdental pappilae | Harmony with remaining teeth of patients suffering from gingival retraction | Feeling of intra-oral incompatibility | Total dental-operating time (hour) | Remarks |
|---|---|---|---|---|---|---|---|---|---|
| Example 1 | Sufficient | Good | Good | Good | Not occurred | Good | Not felt | About 6 | |
| Example 2 | Sufficient | Good | Good | Good | Not occurred | Good | Not felt | About 6 | |
| Example 3 | Sufficient | Good | Good | Good | Not occurred | Good | Not felt | About 6 | |
| Example 4 | Sufficient | Good | Good | Good | Not occurred | Good | Not felt | About 6 | |
| Example 5 | Sufficient | Good | Good | Good | Not occurred | Good | Not felt | About 6 | |
| Example 6 | Sufficient | Good | Good | Good | Not occurred | Good | Not felt | About 6 | |
| Example 7 | Sufficient | Good | Good | Good | Not occurred | Good | Not felt | About 6 | |
| Example 8 | Sufficient | Good | Good | Good | Not occurred | Good | Not felt | About 6 | |
| Example 9 | Sufficient | Good | Good | Good | Not occurred | Good | Not felt | About 6 | |

| | | | | | | | |
|---|---|---|---|---|---|---|---|
| Comparative Example 1 | None | Poor | Poor | Good | Not occurred | Good | Not felt | About 9 | Cutting-off required |
| Comparative Example 2 | Sufficient | Good | Poor | Poor | Not occurred | Poor | Felt | About 6 | |
| Comparative Example 3 | None | Poor | Poor | Good | Not occurred | Poor | Not felt | About 9 | Cutting-off required |
| Comparative Example 4 | Sufficient | Good | Good | Good | Not occurred | Good | Not felt | About 9 | Cutting-off required |
| Comparative Example 5 | Sufficient | Good | Good | Good | Occurred | Poor | Felt | About 6 | |
| Comparative Example 6 | Sufficient | Good | Good | Good | Not occurred | Poor | Felt | About 9 | Cutting-off required |
| Comparative Example 7 | Sufficient | Good | Good | Good | Not occurred | Poor | Felt | About 6 | |
| Comparative Example 8 | None | Poor | Good | Good | Occurred | Poor | Felt | About 9 | Cutting-off required GC acrylic resin tooth |

Example 1 is the typical standard example. In Example 2, the percentage of the major diameter of the hollow to the full major diameter is high. It is understood that the figure 100% means that the hollow is provided over the entire lingual side of an artificial tooth. In Example 3, the percentage of the major diameter of the hollow to the full major diameter is low. In Example 4, the maximum depth of the hollow is increased while the minimum thickness of the cervical segment is decreased. In contrast, the maximum depth of the hollow is decreased while the minimum thickness of the cervical segment is increased in Example 5. In Examples 4 and 5, if the maximum depth of the hollow is increased, then the minimum thickness of the cervical segment should necessarily be decreased, and vice versa. This is because if both the maximum depth of the hollow and the minimum thickness of the cervical segment are increased, then the resulting artificial tooth is unnaturally increased in geometrical magnitude, whereas both are decreased, then the resulting artificial tooth is unnaturally decreased in geometrical magnitude. In Example 6, the percentage of the minimum mesiodistal length of the cervical segment to the maximum mesiodistal length is 100%, a figure indicating that the mesiodistal length from the cervical segment to the incisal edge segment is the same. In Example 7, the percentage of the minimum mesiodistal length of the cervical segment to the maximum mesiodistal length is as low as 64%. In Example 8, the percentage of the major diameter of the cervical segment to the full major diameter is high, whereas in Example 9, the percentage of the major diameter of the cervidal segment to the full major diameter is low.

All the examples gave satisfactory results in terms of the eight aspects, i.e., space for retainers or connectors, color tone of the artificial teeth, shielding effect upon metals, strength of the cervical segments, remaining of food tailings in the interdental pappilae, harmony with the remaining teeth of patients suffering from gingival retraction, feeling of incompatibility in the oral cavities and total operating time.

In Comparative Example 1, the percentage of the major diameter of the hollow to the full major diameter is lower than the lower limit as defined in the appended claims. Due to an insufficient space for a retainer or connector, the retainer or connector cannot be attached in place without cutting the lingual side of the artificial tooth. Required is thus a total operating time of about 9 hours, which is longer by about 3 hours as compared with the case where no cutting is needed. Cutting makes the artificial tooth so thin that no inherent color tone can be obtained and the metallic attachment or connector post may be seen through. In Comparative Example 2, the maximum depth of the hollow is larger than the upper limit whereas the minimum thickness of the cervical segment is smaller than the lower limit. In this example, there is an ample space for a retainer or connector, but no substantial shielding effect upon a metal is obtained; nor is the strength of the cervical segment satisfactory, because of the minimum thickness of the cervical segment being decreased. In Comparative Example 3, the maximum depth of the hollow is smaller than the lower limit whereas the minimum thickness of the cervical segment is larger than the upper limit. In this example, the lingual side of the artificial tooth is needed to be cut due to an insufficient space for a retainer or connector. Cutting makes the artificial tooth so thin that no inherent color tone can be obtained and the metallic attachment or connector post may be seen through. Required is further a total operating time of about 9 hours, which is longer by about 3 hours as compared with the case where no cutting is needed. In Comparative Example 4, the percentage of the minimum mesiodistal length of the cervical segment to the maximum mesiodistal length is higher than the upper limit or 105%, a figure indicating that the mesiodistal length of the cervical segment is longer than that of the incisal edge segment. Due to its unnatural geometry, the artificial tooth cannot possibly be aligned at all. Consequently, there is a need to cut the mesiodistal side of the cervical segment, thus resulting in an increase in the length of time needed for the geometrical correction of the artificial tooth. In Comparative Example 5, the percentage of the minimum mesiodistal length of the cervical segment to the maximum mesiodistal length is lower than the lower limit. For that reason, food tailings were found in an increased gap between the interdental pappilae of the proximal teeth. In Comparative Example 6, the percentage of the major diameter of the cervical segment to the full major diameter is higher than the upper limit. The artificial tooth cannot possibly be aligned at all due to a major diameter of the cervical segment being too much increased. Nor can any harmony with the remaining teeth of a patient suffering from gingival retraction obtained even by cutting. In Comparative Example 7, the percentage of the major diameter of the cervical segment to the full major diameter is lower than the lower limit. Here again, any harmony with the remaining teeth of a patient suffering from gingival retraction cannot be obtained due to a major diameter of the cervical segment being too much decreased. In Comparative Example 8, a partial denture is prepared with the maxillary right-central incisor formed of acrylic resin manufactured by GC Dental. Due to the absence of any hollow, the lingual side of the artificial tooth is required to be cut to assure a space for a retainer or connector. For that reason, any inherent color tone of the artificial tooth cannot be obtained; nor is any shielding effect obtained upon the metallic retainer or connector due to the resulting presence of only a thinly enamelled layer. The cervical segment takes on a plane curved so gently that its minimum mesiodistal length can neither be determined and nor measured. It comes to this that food tailings were found left between a much increased gap between the interdental pappilae of the proximal teeth due to a sharp constriction of the cervical segment. Furthermore, any harmony with the remaining teeth of a patient suffering from gingival retraction cannot be obtained because of the percentage of the major diameter of the cervical segment to the full major diameter being as low as 9%.

It is here to be noted that, while the artificial teeth according to the examples and comparisons are formed of the materials specified in the above table, no further detailed explanation thereto is omitted, since they have no relation to the object of the present invention.

EFFECT OF THE INVENTION

As detailed above, the structure and geometry of the present artificial teeth for anterior teeth portions suitable for making partial dentures and overdentures have the following effects and so make a great contribution to dental treatments.

(1) For the preparation of partial dentures or overdentures, there is a need to combine artificial teeth with retiners, connectors and dental plates (especially metal plates). This then requires to provide therein a space for such purposes and, hence, to cut a part of the basal plane of each artificial tooth. However, since each of the present artificial teeth for anterior teeth portions has a hollow previously formed in its basal plane, there is no need to cut that basal plane, as experienced with the conventional artificial teeth for anterior teeth portions designed for complete dentures. This leads to a reduction in the total operating time, since the desired results are obtained by some slight modifications without need of providing a retainer-receiving hollow by cutting. Furthermore, it is possible to prepare partial dentures or overdentures without being affected by versed skill needed for the cutting of the basal planes of artificial teeth and giving rise to any deformation of the configurations of artificial teeth.

(2) Since the need of cutting the basal planes of artificial teeth is eliminated by the use of the artificial teeth for anterior teeth portions according to the present invention, it is possible to keep the natural color tone inherent thereto. Besides, it is unlikely that a retainer or connector and a dental plate (especially a metal plate) may be seen through the two-layered system of enamel layer and dentine layer or the three-layered structure of enamel, dentine and cervical layers.

(3) When compared with the conventional artificial teeth for anterior teeth portions designed for complete dentures, it is unlikely that food tailing forming dental plaque may remain in the interdental pappilae owing to a decreased gap therebetween. The cervical segments of the present artificial teeth longer than those of the conventional artificial tooth for anterior teeth portions designed for complete dentures are in much well-balanced harmony with the remaining teeth suffering from gingival retraction as well as with the face and age of the patient.

What is claimed is:

1. An artificial tooth for anterior teeth portions including a concave hollow extending from a basal segment to a lingual incisal segment and located in a substantially central segment, wherein:
   a percentage of the major diameter of said hollow to the full major diameter is in a range of 10% to 100%,
   a maximum depth of said hollow is in a range of 0.5 mm to 5.0 mm and
   a minimum thickness of a cervical segment is in a range of 0.1 mm to 5.0 mm, and
   a width and length of said cervical segment being defined in terms of a percentage of the cervical minimum mesiodistal length to the maximum mesiodistal length being in a range of 50% to 100% and a percentage of the cervical major diameter to the full major diameter being in a range of 10% to 50%.

2. An artificial tooth as claimed in claim 1, which is formed of a synthetic resin.

3. An artificial tooth as claimed in claim 1, which is formed of ceramics.

4. An artificial tooth as claimed in claim 1, which is formed of a composite material of a synthetic resin with ceramics.

* * * * *